(12) United States Patent
Kevorkian

(10) Patent No.: US 7,276,492 B2
(45) Date of Patent: Oct. 2, 2007

(54) USE OF ACE INHIBITORS FOR TREATMENT OF PATIENTS SUFFERING FROM BEHAVIORAL DISORDERS

(76) Inventor: Robert C. Kevorkian, 484 Firetown Rd., Simsbury, CT (US) 06070

( * ) Notice: Subject to any disclaimer, the term of this patent is extended or adjusted under 35 U.S.C. 154(b) by 219 days.

(21) Appl. No.: 11/037,564

(22) Filed: Jan. 18, 2005

(65) Prior Publication Data

US 2005/0143444 A1 Jun. 30, 2005

Related U.S. Application Data

(63) Continuation-in-part of application No. 10/276,788, filed as application No. PCT/US01/17451 on May 30, 2001, now abandoned.

(60) Provisional application No. 60/208,637, filed on Jun. 1, 2000.

(51) Int. Cl.
*A61K 31/675* (2006.01)
*A61K 31/40* (2006.01)

(52) U.S. Cl. .......................... 514/91; 514/422; 514/423
(58) Field of Classification Search .................... None
See application file for complete search history.

(56) References Cited

U.S. PATENT DOCUMENTS

| | | | |
|---|---|---|---|
| 2,870,140 A * | 1/1959 | Thompson et al. | 424/725 |
| 4,931,430 A * | 6/1990 | Sudilovsky et al. | 514/19 |
| 5,049,553 A | 9/1991 | Sudilovsky | |
| 5,405,943 A | 4/1995 | Comings | |
| 5,854,290 A | 12/1998 | Arnsten et al. | |
| 6,034,079 A | 3/2000 | Sanberg et al. | |
| 6,043,258 A | 3/2000 | Bymaster et al. | |
| 6,180,678 B1 | 1/2001 | Milgram et al. | |
| 6,187,777 B1 | 2/2001 | Norman et al. | |
| 6,194,432 B1 | 2/2001 | Sheftell et al. | |

OTHER PUBLICATIONS

J. Demark and M. Gemeinhardt, "Anger and its management for survivors of acquired brain injury" Brain Injury, 2002, vol. 16, No. 2, pp. 91-108.

Gil Newburn, Disease Management "Psychiatric Disorders Associated with Traumatic Brain Injury—Optimal Treatment", CNS Drugs Jun. 1998: 9 (6), pp. 441-456.

D.B. Arciniegas, S.N. Harris and K.M. Brousseau, "Psychosis following traumatic brain injury", International Review of Psychiatry, Nov. 2003, 15, pp. 328-340.

T.W. McAllister and R.B. Ferrell, "Evaluation and treatment of psychosis after traumatic brain injury", NeuroRehabilitation 17 (2002), IOS Press, pp. 357-368.

The Merck Manual of Diagnosis and Therapy, 14th ed. (1982), pp. 388-391.

USPDI, 13th ed. (1993), vol. 1, Drug Information for the Health Care Professional, p. 177.

Drug Facts and Comparisons, Facts and Comparisons, Jan. 2000, Renin Angiotensin System Antagonists, pp. 504-518.

Harrison's Principles of Internal Medicine, Eighth Edition, Copyright 1977, McGraw-Hill Book Company, a Blackiston Publication, "335—Traumatic Diseases of the Brain", pp. 1868 and 1869.

PCT International Search Report for PCT/US01/17451, dated Jul. 27, 2001.

PCT International Preliminary Examination Report for PCT/US01/17451, dated Apr. 26, 2002.

Email search report from Information and Education Services, University of Connecticut Health Center Library (report by Hongjie Wang) re Treatment of Behavioral Disorder Following Traumatic Head Injury, Dated Nov. 24, 2004 (31 pages).

* cited by examiner

*Primary Examiner*—Raymond J. Henley, III
(74) *Attorney, Agent, or Firm*—Cantor Colburn LLP

(57) ABSTRACT

A method for the treatment of a patient suffering from an endogenous behavioral disorder in order to ameliorate at least some behavioral aspects of the disorder, the method comprising administering to the patient a therapeutic quantity of at least one ACE inhibitor. Behavioral aspects of endogenous disorders such as attention deficit disorder (ADD), obsessive-compulsive disorder (OCD), oppositional explosive defiant disorder (OEDD), anxiety and panic disorders (APD) and temper, rage and outburst behavior disorder (TROBD), are ameliorated by a regimen of ACE inhibitor.

9 Claims, No Drawings

USE OF ACE INHIBITORS FOR TREATMENT OF PATIENTS SUFFERING FROM BEHAVIORAL DISORDERS

CROSS REFERENCE TO RELATED APPLICATION

This application is a continuation-in-part of, and claims priority of, U.S. application Ser. No. 10/276,788 entitled "Use of Ace Inhibitors For Treatment of Patients Suffering From Behavioral Disorders", filed on Nov. 20, 2002 in the name of Robert C. Kevorkian, now abandoned, which application is based on and claims priority of Patent Cooperation Treaty Application Serial Number PCT/US01/17451, filed May 30, 2001, which in turn claims priority of U.S. provisional application No. 60/208,637 filed Jun. 1, 2000.

BACKGROUND OF THE INVENTION

1. Field of the Invention

Angiotensin converting enzyme inhibitors (ACE inhibitors) are known to be useful for treatment of a variety of cardiovascular ailments such as hypertension, heart failure, myocardial infarction, left ventricular dysfunction and diabetic nephropathy. ACE inhibitors are believed to inhibit the action of angiotensin-converting enzyme (ACE) in the body in its conversion of angiotensin I, a relatively inactive peptide, to angiotensin II, a powerful vasoconstrictor and stimulant of the adrenal cortex for the secretion of aldosterone, which is normally associated with fluid retention. Angiotensin I is the product of the action of renin, which is produced by the kidneys, on angiotensinogen (a globulin of plasma). The action of an ACE inhibitor, by reducing conversion of angiotensin I, relieves vasoconstriction and reduces aldosterone secretion. It also provides negative feedback on renin release, which is also believed to decrease aldosterone secretion. ACE inhibitors also include angiotensin II antagonists.

Another possible basis for the effectiveness for ACE inhibitors is that ACE is identical to bradykininase (kininase II), which acts on bradykinin. Bradykinin stimulates prostaglandin biosynthesis and it is believed that ACE inhibitors also inhibit bradykininase and thereby increase bradykinin levels. ACE inhibitors thus stimulate the biosynthesis of prostaglandin, which is a vasodilator and which may contribute to the pharmaceutical effects of ACE inhibitors.

The physiological effects associated with ACE inhibitors include increases in serum potassium and sodium and fluid loss, a reduction of peripheral arterial resistance in hypertensive patients and an increase in cardio output with little or no change in heart rate. There is also an increase in renal blood flow, reduction in blood pressure and an improvement in maximal exercise tolerance in patients with heart failure.

ACE inhibitors are characterized as peptides that fall into three groups: sulfhydryl-containing (e.g., captopril), dicarbocyl-containing (e.g., enalapril, lisinopril, benazepril, quinapril, moexipril, trandolapril, and ramipril), and phosporous-containing (e.g., fosinopril). Other known ACE inhibitors are enalaprilat, irbesartan, losartan potassium, valsartan, zofenapril and ceranapril. The pharmaceutical dosages and administration of the various ACE inhibitors are known to those of ordinary skill in the art. Typically, the compositions are administered orally.

2. Related Art

In *Drug Facts and Comparisons*, January 2000, published by Facts and Comparisons, St. Louis, Mo., certain "adverse reactions" of various ACE inhibitors are shown, including reactions pertaining to the central nervous system. Some of these include confusion, depression, malaise, nervousness and anxiety. When the incidence of these reactions were given, they almost all were reported in less than one percent of the persons treated. In addition, the following reactions were reported at incidences of less than one percent of the persons treated: dream abnormality (in connection with enalapril); memory disturbance, mood change and behavior change (in connection with fosinopril); irritability (in connection with lisinopril) and mood changes (in connection with moexipril).

U.S. Pat. No. 5,049,553 entitled "Method For Preventing or Treating Symptoms Resulting From Closed Head Injuries Employing an ACE Inhibitor" issued on Sep. 17, 1991 to A. Sudilovsky. The '553 patent discloses the administration of an ACE inhibitor to treat symptoms brought on by head trauma which causes unconsciousness for twenty minutes or more. The stated symptoms include rages as well as memory loss, headache, dissociation of thought and depression, among others. See column 1, lines 60-64 and column 1, line 65 to column 2, line 17. The '553 patent also notes that ACE inhibitors are useful for treating hypertension; see the art cited at column 1, lines 27 to 59 and column 2, lines 18-20.

SUMMARY OF THE INVENTION

Generally, the present invention provides a method for the treatment of patients suffering from an endogenous behavioral disorder by administering to the patient a therapeutic quantity of at least one ACE inhibitor, such as a dicarbocyl-containing ACE inhibitor, e.g., lisinopril. As used herein and in the claims, "endogenous" behavioral disorders are disorders not associated with or resulting from traumatic head injury or other trauma, but rather those which find their etiology solely in non-trauma induced conditions such as psychological conditions or illnesses, hormonal imbalances, or the like.

Specifically, in accordance with the present invention there is provided a method for the treatment of a patient who suffers from an endogenous behavioral disorder in order to ameliorate at least some behavioral aspects of the disorder, comprising administering to the patient at least one ACE inhibitor at a frequency and dosage sufficient to ameliorate at least some behavioral aspects of the disorder.

The endogenous behavioral disorder may be one which is associated with the elevation of blood pressure. For example, the endogenous behavioral disorder may be one selected from the group consisting of attention deficit disorder (ADD), obsessive-compulsive disorder (OCD), oppositional explosive defiant disorder (OEDD), anxiety and panic disorders (APD) and temper, rage and outburst behavior disorder (TROBD).

In accordance with one aspect of the present invention, the method comprises administering a dicarbocyl-containing ACE inhibitor, e.g., lisinopril.

In another aspect of the present invention, the at least one ACE inhibitor is administered to the patient by oral ingestion, e.g., by oral ingestion of at least one orally-ingestable, premeasured unit dosage.

A particular aspect of the present invention provides a method for the treatment of a patient who suffers from temper, rage and outburst behavior disorder (TROBD), the method comprising administering to the patient at least one ACE inhibitor as described above, e.g., administering a dicarbocyl-containing ACE inhibitor, e.g., lisinopril.

DETAILED DESCRIPTION OF THE INVENTION AND PREFERRED EMBODIMENTS THEREOF

The present invention is based on the observation that beneficial behavioral modification effects are produced by ACE inhibitors in patients suffering from endogenous behavioral disorders, making ACE inhibitors useful for certain patients for whom they might not otherwise be prescribed. These beneficial effects may be manifested as behavioral improvements in people, both children and adults, who suffer from endogenous disorders including attention deficit disorder (ADD), obsessive compulsive disorder (OCD), oppositional explosive defiant disorder (OED), anxiety and panic disorders (APD), and impulsive temper, rage and outburst behavior disorder (TROBD). Accordingly, the present invention provides a new method for the treatment of persons with such endogenous disorders, comprising the administration of one or more ACE inhibitors in a therapeutic regimen that may parallel a regimen that would be used in those patients for the treatment of cardiovascular disease in which the ACE inhibitor would be indicated. Without wishing to be bound by any particular theory, it is believed that certain endogenous physiological conditions which are controllable through the use of ACE inhibitors are related to certain behavioral problems. For example, the production of angiotensin II and its associated elevation of blood pressure appear to be correlated with outbursts of rage, anger and even violence. In two patients who volunteered to be studied, it was found that significantly elevated blood pressure accompanied temper outbursts. It is therefore believed that controlling these phenomena can help the patient control the undesired behavior.

This invention is expected to be useful not only for human patients but also for non-human mammalian patients whose cardiovascular systems are known to be affected by ACE inhibitors in a manner analogous to the reactions of humans to ACE inhibitors.

EXAMPLE 1

A twelve-year old human male had an eight-year history of uncontrollable temper, rage and violent outburst behavior, i.e., was a patient suffering from TROBD. The TROBD was an endogenous behavioral disorder. The patient was placed on a regimen of the dicarbocyl-containing ACE inhibitor lisinopril, 10 mg per day, oral administration. Prior to medication, the patient displayed two to four episodes of fit or rage and/or violent behavior per week, each lasting approximately twenty minutes per episode. When confined to his room, the patient would act out with banging and stomping. Episodes were accompanied by physiological changes including dilation of pupils, expressionless face and a rise in blood pressure. Prior treatments with methylphenidate (e.g., Ritalin), dextroamphetamine (e.g., Dexedrine) and counseling were ineffective to provide adequate relief.

With lisinopril medication as noted above over a period of about four weeks, definite changes in behavior were evident. Episodes were reduced in duration and frequency to episodes of approximately five to ten minutes with a frequency of approximately one per week, without violent outburst. At home, he retreated from a situation triggering the event to his room, where he remained quiet.

The patient exhibited improved behavior throughout a therapeutic regimen extending for a period of approximately two and one-half months. Under treatment, there was no noticeable dilation of pupils and blood pressure did not go over 128/64 during the three most marked temper-related episodes in that period. Each of the three episodes occurred at school. In one episode, the patient was working on a computer and refused to give up his work station when his allotted time had been used up. The teacher reported that the patient was verbally resistive and spilled his milk, but did not act out violently and, when so instructed, walked to the principal's office without being physically coerced. A second episode was triggered when the patient was asked to make up a class he had missed. He refused to go to the class but voluntarily moved himself to a "cooling room" to allow his temper to subside. He again, when so instructed, walked to the school office without being physically coerced. In a third episode, the patient was asked to leave the classroom because he would not stop talking during a quiet time. In this case, there was a limited degree of acting out in that, while sitting in a chair, he kicked a desk which was knocked over. He then allowed himself to be escorted by police officers to the school office without being physically coerced. In the office, he kicked another desk and was taken by ambulance to a children's hospital for evaluation. The degree of violence in all of these episodes, including the third episode, was significantly reduced compared to the patient's behavior prior to treatment with the ACE inhibitor.

EXAMPLE 2

The grandfather of the subject of Example 1 also had a long history of endogenous temper, rage and outburst behavior disorder (TROBD). After receiving an ACE inhibitor for treatment of his high blood pressure, his outbursts were markedly reduced.

What is claimed is:

1. A method for the treatment of a patient who suffers from an endogenous behavioral disorder selected from the group consisting of attention deficit disorder (ADD), oppositional explosive defiant disorder (OEDD) and temper, rage and outburst behavior disorder (TROBD) in order to ameliorate at least one behavioral aspect of the disorder, the method comprising administering to the patient at least one angiotensin converting enzyme ("ACE") inhibitor at a frequency and dosage sufficient to ameliorate the at least one behavioral aspect of the disorder.

2. A method for the treatment of a patient who suffers from endogenous temper, rage and outburst behavior disorder (TROBD) in order to ameliorate at least one behavioral aspect of the disorder, the method comprising administering to the patient at least one angiotensin converting enzyme ("ACE") inhibitor at a dosage and frequency sufficient to ameliorate the at least one behavioral aspect of the disorder.

3. The method of claim 1 or claim 2 wherein the patient is a human being.

4. The method of claim 1 or claim 2, comprising administering a dicarbocyl-containing ACE inhibitor as the at least one ACE inhibitor.

5. The method of claim 4 wherein the patient is a human being.

6. The method of claim 1 or claim 2, comprising administering lisinopril as the at least one ACE inhibitor.

7. The method of claim 6 wherein the patient is a human being.

8. The method of claim 1 or claim 2 wherein the at least one ACE inhibitor is administered to the patient by oral ingestion of at least one orally-ingestable, pre-measured unit dosage.

9. The method of claim 8 wherein the patient is a human being.

* * * * *